United States Patent [19]

Brewer et al.

[11] Patent Number: 4,810,629

[45] **Date of Patent: * Mar. 7, 1989**

[54] IDENTIFICATION OF VIRAL ASSOCIATED IMMUNOREACTANTS IN BIOLOGICAL FLUIDS

[75] Inventors: John H. Brewer, Gibson Island, Md.; Terry L. Foster, Abilene, Tex.

[73] Assignee: Fairleigh Dickinson Laboratories, Inc., Abilene, Tex.

[ * ] Notice: The portion of the term of this patent subsequent to Dec. 4, 2001 has been disclaimed.

[21] Appl. No.: 780,628

[22] Filed: Sep. 26, 1985

Related U.S. Application Data

[60] Continuation-in-part of Ser. No. 645,665, Aug. 30, 1984, Pat. No. 4,696,907, which is a division of Ser. No. 493,413, May 10, 1983, Pat. No. 4,486,540, which is a continuation-in-part of Ser. No. 323,762, Nov. 23, 1981, abandoned, which is a division of Ser. No. 170,143, Jul. 18, 1980, Pat. No. 4,331,650.

[51] Int. Cl.$^4$ .................. G01N 33/546; G01N 33/547

[52] U.S. Cl. ........................................ 435/5; 436/524; 436/527; 436/528; 436/531; 436/532; 436/533; 436/534; 436/511

[58] Field of Search ............... 436/513, 524, 527, 528, 436/531, 532, 533, 534, 511; 435/5

[56] References Cited

U.S. PATENT DOCUMENTS

| | | | |
|---|---|---|---|
| 4,060,597 | 11/1977 | Sato | 436/534 |
| 4,197,088 | 4/1980 | Meserol | 436/534 |
| 4,452,734 | 6/1984 | Larson | 530/396 |

*Primary Examiner*—Robert J. Warden
*Assistant Examiner*—Robert Benson
*Attorney, Agent, or Firm*—Kane, Dalsimer, Sullivan, Kurucz, Levy, Eisele and Richard

[57] ABSTRACT

The disclosure is of an improved method for the in-vitro detection and identification of viral associated immunoreactants in biological fluids including cell cultures. The improvement comprises admixing the fluid with solid, porous carrier particles bearing surface adsorbed, known immunological homolog/surfactant complexes. An agglutination reaction indicates the presence of immunoreactant corresponding to the surface adsorbed homolog.

8 Claims, 1 Drawing Sheet

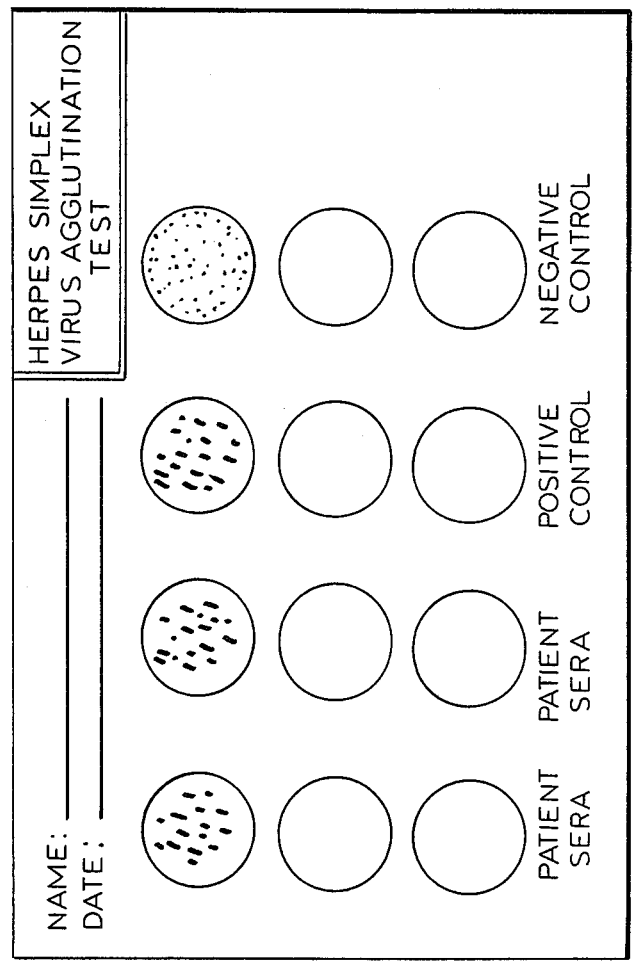

IDENTIFICATION OF VIRAL ASSOCIATED IMMUNOREACTANTS IN BIOLOGICAL FLUIDS

BACKGROUND OF THE INVENTION

CROSS-REFERENCE TO RELATED APPLICATION

This application is a continuation-in-part of application Ser. No. 645,665 filed Aug. 30, 1984 (now U.S. Pat. No. 4,696,907) which was a division of application Ser. No. 493,413 filed May 10, 1983 and now U.S. Pat. No. 4,486,540, which was a continuation-in-part of application Ser. No. 323,762 filed Nov. 23, 1981, now abandoned, which was a division of application Ser. No. 170,143 filed July 18, 1980 and now issued as U.S. Pat. No. 4,331,650.

FIELD OF THE INVENTION

The invention relates to an in-vitro method of identifying viral associated immunoreactants in biological fluids.

BRIEF DESCRIPTION OF THE PRIOR ART

Immunoglobulins are modified forms of the blood protein known as globulin and include antibodies. They are found in the body fluids of vertebrates following their sensitization by systemic exposure to a protein (antigen) foreign to the vertebrates evolutionary chemistry.

A wide variety of procedures are known for the immunoassay of immunoglobulins, i.e.; the determination of the quantity of immunoglobulins in a given biological fluid, using immuno-chemical technique. Immunochemistry is chemistry classically concerned with the physical interaction between "antigens" and "antibodies" which are the "immunoreactants" participating in an immunochemical reaction.

"Antigens" are high molecular weight compounds, usually protein or protein-polysaccharide complexes, which upon entry in the blood stream of vertebrate animals stimulate the transformation of the small lymphocytes of the B-type into lymphoblasts. The lymphoblasts secrete antibodies which are proteins possessing reactive sites specifically complimentary to a reactive feature or site on the stimulating antigen. Antibodies generally have the property of rendering the antigen harmless to the host organism, by occupying the immunologically active sites on the antigen particles or molecules, and sometimes also by forcing precipitation or agglutination of the antigen, or by other protective mechanisms.

The words "precipitation" and "agglutination" differ in that precipitation refers to formation of a particulate or agglomerate solid from molecules initially in solution or, particularly in immunology, dissolved in biological fluids. Agglutination refers to formation of an agglomerate from particulate substances initially suspended in a fluid. When suspended particles react with dissolved molecules to form an agglomerate, the term "agglutination" is usually applied. In addition, the word "agglomeration" is used as a general term encompassing both pairing of particles and clumping of a large multiplicity of particles.

In some applications it becomes difficult or meaningless to maintain the classical distinction between antigen and antibody, because in many regards the relation between antigen and antibody is reciprocal and each precipitates or agglutinates the other. The basis for the distinction resides in the history of the particular substances, and this can become irrelevant outside the original antibody-generating organism, for example in reagent applications. For this reason the antigen-antibody relationship may be advantageously described in this reciprocal way: an antibody is the "immunological homologue" of the antigen which produced it, and vice versa. An antibody and its corresponding antigen are thus immunological homologs of each other. They may also be said to be immunologically homologous to each other.

In any event, the immunological antigen-antibody relationship forms the basis for immunoassay of either immuno-"reactant". Procedurally the various known techniques of immunoassay for the immunoreactants (antigen, antibody), i.e.; radioimmunoassay, fluorescent immunoassay and enzyme immunoassay are substantially identical. Each technique comprises, in general, immobilizing one of the immunoreactants, labelling one of the immunoreactants with a marker or tag to monitor its presence and reacting the immobilized immunoreactant with the free immunoreactant and measuring the degree of reaction through monitoring of the labelled immunoreactant. The difference between the various techniques resides in utilization of different reagents as markers or tags for visualization and quantification.

Viruses which invade vertebrate circulatory systems are antigenic in character or carry with them antigens, sensitizing the animal. The antibodies produced by the host animal in response to the presence of these antigens belong to a class of immunoglobulins known as immunoglobulin G (IgG) or immunoglobulin M (IgM). These proteins may be heterogeneous mixtures of structurally similar but diverse proteins. Any in-vitro detection or immunoassay method based on immunoreaction of the IgG or IgM with an immunoreactant may depend for accuracy on a protocol which may not account for all of the diverse immunoglobulin molecules, but just a portion of the mixture. Further, IgM and IgG are protective antibodies produced by an organism to counteract antigens related to disease. In the process, the host organism may continue to produce "protective" types of antibody even after the disease state or entity has been eliminated, thereby obtaining immunity to reinfection but complicating detection of active antigen in any known test method. For these and other reasons, the prior art immunoassay test methods have not been entirely satisfactory for the detection and assay of virus related or produced immunoreactants. Avidity and accuracy of the known test procedures are at best only crude approximations of what is required for optimum results and usefulness.

The method of the present invention is an improvement over prior art immunoassays for the detection and assay of virus related antigens and corresponding antibodies in that it is highly accurate, rapid, easily carried out with a minimum of training and practice and economical. The immunoassay of the invention may be carried out without the need for expensive laboratory facilities; even in the physician's office.

The method of the invention also requires only small biological fluid samples for testing (less than 0.5 ml), providing the patient with considerably decreased discomfort and loss of time. Once the fluid sample is obtained the patient need not wait long for results. Automation of the procedure will enable the physician to increase the number of patients he can test in a given time period.

The method of the invention may be used to assay titer levels of specific IgG and IgM, thereby enabling the physician to monitor a patient for re-infection. this is highly advantageous in the treatment of sexually transmitted viral infections.

The method of the invention is especially useful in the diagnosis and treatment of sexually transmitted viral infections, most especially Herpes virus infections, by the assay for related antigens and antibodies.

In recent months, public attention has been focused on the major increase in the number of infections reported in humans and attributed to the herpes simplex virus (HSV), particularly the type 2 virus. The type 2 virus is generally associated with genital infections, i.e.; a heretofore incurable venereal disease spread by sexual contact with an infected individual. The type 1 herpes simplex virus is also prevalently hosted in humans and is more often associated with symptomatic lesions in the oral zones.

The need for rapid diagnosis of the infection, especially in pregnant females, has received widespread attention. Presently, the most widely accepted method for detecting HSV infection is by conventional tissue culture in a susceptible cell line and demonstration of characteristic cytopathic effect. This is often confirmed by demonstrating in vitro neutralization or plaque reduction of the virus using conventional hyperimmune animal antisera or by specific immunological staining procedures, some of which employ monoclonal antibodies. These procedures are labor-intensive, time-consuming, and expensive, often requiring special technical expertise not available in many laboratories. Newer procedures based upon enzyme immunoassays are simpler to perform, but continue to be time-consuming, expensive, and require destruction of the tissue culture for performance of the test.

The method of the present invention is useful to identify the presence of herpes simplex virus in infected cell cultures. The test is performed in 15 minutes, requires no expensive instrumentation, requires little hands on time, and requires little technical training. It is more cost effective than other HSV confirmatory procedures in that it is not labor-intensive and does not require destruction of the tissue culture for assay. Those laboratories familiar with particle agglutination testing, or various coagglutination procedures, already possess expertise to perform and interpret this test format.

SUMMARY OF THE INVENTION

The invention comprises a method of determining the presence or the absence of a viral associated immunoreactant in a biological fluid, which comprises;

A. providing an extra-corporeal specimen of the biological fluid;

B. providing an aqueous dispersion of solid, porous carrier particles having adsorbed thereon a complex of the formula:

A X-Y wherein X represents a hydrophilic, polar moiety, Y represents a hydrophobic non-polar moiety and A is the immunological homolog of the viral associated immunoreactant being determined for;

C. admixing the specimen provided with the aqueous dispersion; and

D. observing the admixture for an agglutination reaction;

wherein a positive agglutination reaction is indicative of the presence of the viral associated immunoreactant and the absence of an agglutination reaction is indicative of the absence of the viral associated immunoreactant in the biological fluid.

The method of the invention is useful for identifying viral associated antigens and/or antibodies present in biological fluids for viral disease sensitized vertebrates, including humans.

The method of the invention is of especial use for the diagnosis and treatment of sexually transmitted viral infections, particularly Herpes simplex virus, referred to at times herein as "HSV".

The term "biological fluids" as used herein means fluids associated with a living vertebrate, such as nasal, bronchial, middle ear, gastric, lachrimal and like secretions of biological origin, especially blood serums and secretions of open sores and lesions. Also included within the term are laboratory cultures of organisms obtained from such fluids.

The invention also comprises test reagents employed in the method of the invention.

BRIEF DESCRIPTION OF THE DRAWING

The FIGURE is a plan view of a laboratory test card device showing the results of an identification test carried out according to the method of the invention.

DETAILED DESCRIPTION OF THE PREFERRED EMBODIMENTS OF THE INVENTION

The basic principle of the method of the invention requires one to attach an analyte, usually the antigen, to microscopic particles. When this is spread in a circle on a slide or card and rotated, it exhibits a smooth, homogeneous appearance. However, when mixed with reciprocal analyte, usually specific antibody, the reagent particles aggregate, forming macroscopically visible clumps. Within limits, the degree of clumping is directly proportional to the unknown analyte concentration. Accordingly, an initial step in the method of the invention is the provision of an aqueous dispersion of finely divided, solid, porous, carrier particles having adsorbed thereon a given and known immunoreactant corresponding to the immunological homolog counterpart of the immunoreactant to be determined (presence identified). Solid carrier particles employed are represented by finely divided particles of silicia, ion-exchange resins, alumina, kaolin, bentonite, graphite, charcoal, quartz, protein particles, organic polymeric resins, latex particles and like water-insoluble material. Preferred are non-polar materials such as carbon black, charcoals, graphite, organic resins, paraffin, synthetic organic polymers, talc and the like since these non-polar materials form excellent homogeneous dispersions in water. The particles are advantageously within an average size range of from 0.5 to 15 $\mu$m, preferably 0.5 to 2.0 um in diameter and the aqueous dispersions prepared therefrom advantageously contain a concentration of the solid particles within the range of from about 0.005 to 0.5 percent by weight, preferably about 0.02 percent.

The solid carrier particles employed as reagents in the method of the invention have adsorbed on their surfaces, a given and known complex of a specific immunological homolog of the immunoreactant to be identified and a surfactant of the formula (I) given hereinafter. The technique of adsorption comprises an admixture of the complex with the insoluble carrier material. The complex is surface adsorbed on the carrier particles over a period of time under specific conditions. The degree of adsorption and the time required for adsorption will vary depending on the physical nature of the carrier particles, but may be determined by a conventional technique such as by a trial and error technique.

The immunological homolog/surfactant complex possesses surfactant properties to promote their adsorption on the non-polar particle surfaces. Surprisingly the complexes retain the biochemical activity of the immunoreactant moiety of the complex. The complex is resistant to desorption from the surface of the carrier particle once adsorbed thereon. Resistance to desorption ultimately results in amplification of the agglutination reaction which may occur when the carrier particles with adsorbed allergen are exposed to the analyte, as hereinafter described more fully.

The term "surfactant" as used herein is a contraction of "surface-active agent" and is a broadly descriptive term used to describe a chemical compound which is (1) soluble in at least one phase of the system, (2) has an amphipathic structure, (3) the molecules of which form oriented monolayers at phase interfaces, (4) exhibits an equilibrium concentration as a solute at a phase interface, greater than its concentration in the bulk of the solution, (5) forms micelles when the concentration as a solute in solution, exceeds a characteristic limiting value and (6) exhibits some combination of the functional properties of detergency, foaming, wetting, emulsifying, solubilizing and dispersing. In view of the surfactant character of the complexes formed and used in the method of the invention, it is surprising that they actually enhance or amplify the agglutination reaction described more fully hereinafter.

The surfactant immunological homolog complex adsorbed on carrier particles and used in the present invention may be prepared by bringing together the immunological homolog with a compound of the general formula:

$$X-Y \quad (I)$$

wherein X represents a hydrophilic, polar moiety and Y represents a hydrophobic, non-polar moiety. The compound of formula (I) will complex with the immunological homolog according to the reaction scheme:

$$A + X-Y \longrightarrow A\ X-Y$$
$$(I) \qquad\qquad (II)$$

wherein X and Y are as previously defined and A represents the polar immunological homolog molecule. It will be observed from the above reaction scheme that the product complex (II) is one wherein the hydrophilic or polar moiety X of the compound (I) is turned or oriented toward the polar immunological homolog molecule and the hydrophobic, non-polar Y moiety is oriented away from the immunological homolog molecule. When the complex product (II) is mixed in a solute with the solid, non-polar carrier particles, the non-polar Y moiety orients toward the non-polar surface of the carrier particle. This, of course is ideal for adsorption of the complex (II) from the aqueous mixture since the polar portion X orients toward the aqueous phase (polar phase) and the non-polar portion Y is most readily adsorbed by the non-polar surface of the carrier particle.

Immunological homologs of antigens associated with viruses, i.e.; antibodies are obtainable by immunological methods well known to those skilled in the art. Many of such antibodies are commercially available. Preferably the antibodies employed to form the complexes of Formula (II) described above are relatively pure and free of contaminants. The antibodies are advantageously mixed with the compound (I) in a proportion of from about 1.0 to 50.0 mg/ml. of antibody to 0.1 to abut 1.0 mg/ml. of the compound of formula (I). Following admixture, the resulting mixture may be incubated for from 15 to 60 minutes at room temperatures to allow the desired complex (II) to form.

Representative of compounds of the formula (I) are those in which the polar group X is selected from phosphato, carboxylic, sulphato, amino, hydroxyl, choline and like groups and the non-polar group Y is selected from a saturated or unsaturated aliphatic hydrocarbon group (such as alkyl or alkylene), an aliphatic hydrocarbon group substituted by at least one aromatic or cycloaliphatic group and the like. Preferably, the compound of formula (I) is a phospholipid such as lecithin, phosphatidylethanolamine, lysolecithin, lysophosphatedylethanolamine, phosphatidylserine, phosphatidylinositol, sphingomyelin, cardiolipin, phosphatidic acid, the cerebrosides and the like. In a most preferred embodiment of the process, a mixture of compounds of the formula (I) are employed, at least one of which is a phospholipid as described above and the other or others are non-phospholipids such as stearylamine, dicetyl phosphate, cholesterol, tocopherol and the like.

The surfactant complex of immunological homolog and a compound of the formula (I) is advantageously formed by bringing the homolog and compound (I) together in the presence of an inert solvent.

The term "inert solvent" as used herein means a solvent for the compound of formula (I), which will not interfere with or otherwise adversely affect the desired course of the method of the invention. Representative of such solvents are a wide variety of ethers, esters, alcohols, ketones, hydrocarbons (aromatic and aliphatic including fluorocarbons), and silicones in which an aqueous phase does not have an appreciable solubility. The solvents may be used either singly or in admixture. Preferred as the inert solvent are the alcohols such as ethanol.

Those skilled in the art will appreciate that in forming the surfactant complex of formula (II) given above in the presence of an alcohol, the immunological homolog may be denatured and thereby rendered biologically inactive. In fact, in the presence of an alcohol denaturization does occur and the desired surfactant complex of homolog and compound (I) will precipitate from the alcoholic mixture as denaturization occurs. The desired precipitate of the complex (II) is conveniently then separated from the alcoholic mixture by centrifugation and dissolved in an aqueous solution to re-nature the immunological homolog and re-activate its biological activity. The re-natured complex of formula (II) may then be adsorbed on the surface of the carrier particles as described above.

In the next step of the method of the invention, an extra-corporeal specimen of biological fluid is obtained from the individual suspected of hosting a virus. The specimen may then be mixed with a similar volume of the aqueous dispersion of carrier particles bearing the immunological homolog material and the resulting mixture observed for agglutination of the particles.

To understand further the method of the invention, reference may be now made to the accompanying drawing. The FIGURE is a plan view of a laboratory test card device showing the results of a virus identification test carried out according to the method of the invention. The test card, as initially provided may be smooth, well calendered paper or cardboard with a water-wettable, water-impermeable surface. The test card preferably has a white color to contrast with the charcoal/complex particles employed in the test method. Indicia are provided on the card surface to identify the particular test, i.e.; a HSV test in this instance. Space is provided for a date and patient identification. Eight test spots or sites are outlined and identified by indicia as to the test being performed. As shown in the FIGURE, one row of two sites are provided for testing patient sera, one site for a positive control and one site for a negative control. It will be appreciated that the particular arrangement or system of the test card shown in the FIGURE is for exemplification and is not limiting.

On the test card of the FIGURE, from 0.01 to 0.05 ml of fluid for testing was deposited on each of two test sites identified as "patient". On the one test site labelled "positive control", 0.01 to 0.05 ml of fluid from a fluid know to contain virus is deposited and to one site labelled "negative control", 0.01 to 0.05 ml of fluid know to be free of virus is deposited. To each site there is then deposited 0.01 to 0.05 ml of an aqueous suspension of carrier/complex particles as described above. The test card is then placed on a laboratory shaking machine and shaken at 120 gyrations per minute for from 4 to 15 minutes. During this period the mixture on the test sites are observed. Clumping or agglutination of the suspended particles as shown in the two "patient" zones and in the site of the "positive control" are evidence of an immunoreaction and the absence of clumping or agglutination as shown in the "negative control" site is evidence of no immunoreaction. In the example of the FIGURE, one may conclude that the patient is infected with a virus associated with antigen which is the immunological homolog of the immunoreactant used to form the particle carrier/complex employed in the method of the invention. If no agglutination had occurred at the test sites identified for the patient, one could conclude that viral infection was absent in the patient.

Although the above-described test procedure may be carried out at room temperatures, it is preferred to incubate the reactants during shaking at a temperature of circa 25° C. to 37° C. in a humid atmosphere.

HERPES AGGLUTINATION TEST

The invention will now be described in relation to a particularly preferred embodiment, which comprises the immunoassay of herpes simplex virus associated antigen. In the preferred embodiment, termed a Herpes Agglutination Test (HAT), charcoal is the preferred particle carrier and has clear advantages for accuracy and avidity of testing.

The Herpes Agglutination Test (HAT) is a rapid, macroscopic, charcoal agglutination test especially useful for screening tissue cultures for the presence of herpes simplex virus (HSV). It may be used by persons or laboratories desiring a rapid means of confirming that cytopathic effect (CPE) observed in tissue culture is due to the presence of herpes simplex virus.

SPECIMEN COLLECTION AND HANDLING

The providing of specimens for herpes viral isolation and identification is a critical part of the procedure and should be performed using careful and known sampling procedures. Specimens should be collected as soon as possible after onset of patient symptoms and transported to the laboratory for tissue culture inoculation as soon as possible. Aseptic technique should be employed in all procedures, and samples should not be subjected to repeated freezing and thawing.

Genital Lesions, Oral Lesions Skin Lesions, and Vesicle Fluids

Generally one of the three stages of lesion development is encountered, namely, vesicular, ulcerative, or crusted-postular. The best opportunity for viral isolation occurs with the vesicular lesion. This fluid can be collected aseptically with a 1.0 ml, or smaller, syringe with small-guage needle. It can also be collected by carefully puncturing the vesicular lesion and absorbing fluid onto a dry, sterile swab. If the vesicle is broken, vigorously swab the base of the lesion. The swab or fluid should be transferred to a transport medium and the syringe rinsed with a small volume of medium.

The ulcerative lesion should be opened to expose the base of the lesion. Cell material at the lesion base can be collected by scraping with a sterile scapel. Viable cells may contain infections HSV, and these should be placed into transport medium. Care should be taken not to produce bleeding.

The crust and/or pus should be removed from this type of lesion. As above, cell material at the lesion base can be collected by scraping with a sterile scapel. Viable cells, which may contain infections HSV, should be transferred to transport medium. Care should be taken not to produce bleeding.

Eye Exudates

Absorb eye exudate onto a sterile, moist swab by rubbing the palpebral conjunctiva. Place the swab into transport medium.

Throat Specimens

Rub tonsils and back of pharynx with a dry, sterile swab. Insert swab into transport medium.

Throat washings are collected by having the patient gargle with 10 ml of sterile saline and expectorate into a sterile cup with a cover. Due to the dilution of this sample, it should be immediately sent for direct inoculation into cell culture containing appropriate antibiotics.

Spinal Fluid

Collect 0.5 to 2.0 ml of spinal fluid.

Autopsy or Biopsy Specimens

Fresh tissue should be obtained from the suspect site. It should not be placed into preservative, but should be teased, diced, or ground with sterile instruments and placed into transport medium. Precautions should be taken to prevent aerosolization of samples.

Swab-transport Systems

Most specimens are currently collected and transported to the laboratory using a swab-transport tube system. The transport medium is designed to prolong infectivity of HSV prior to cell culture inoculation, and the swabbed specimen is immediately placed into one of these transport media. If the transport medium is to be inoculated into tissue culture on the day of sampling, it can be maintained at room (20° C.) or refrigerator (4°-7° C.) temperature. For shipping, the transport medium should be in a wet ice container (4°-7° C.), but should not be frozen. Specimens in transport medium should not be frozen; however, if there is delay getting the specimen into transport medium, it should be stored at −70° C.

Many swab-transport systems are known and useful to provide the biological fluid for testing according to the method of the invention. A large number of such systems are available commercially. For more detailed descriptions of transport media, tissue culture inoculation and HSV isolation see Lennette, D. A., J. L. Melnick, and P. B. Jahrling. 1980. Clinical Virology, pp. 760-771. In E. H. Lennette, A. Balows, W. J. Hausler, Jr., and J. P. Truant (eds.), Manual of Clinical Microbiology, 3rd Edition. American Society for Microbiology, Washington, D.C.; Lennette, D. A. and E. T. Lennette. 1981. *A User's Guide to the Diagnostic Virology Laboratory.* University Park Press, Baltimore, Md.; and Rawls, W. E. 1979. Herpes Simplex Virus Type 1 and 2 Herpes Simiae, pp. 309, 373. In E. H. Lennette and N. J. Schmidt (eds.), Diagnostic Procedures for Viral, Rickettsial, and Chlamydial Infections. American Public Health Association, Washington, D.C.

The collected and transported biological fluid specimens are preferably inoculated into cell line culture media for culturing of any HSV present in the collected specimen. The following cell cultures have been used successfully and proven to possess no cross-reactivity with the charcoal anti-HSV reagent, used in the method of the invention.

| Name | ATCC # | Derivation | Type |
|---|---|---|---|
| BS-C-1 | CCL26 | Monkey Kidney | Epithelial |
| Flow 7000 | None | Human Embryonic Foreskin | Fibroblast |
| MRC-5 | CCL171 | Human Embryonic Lung | Fibroblast |
| SIRC | CCL60 | Rabbit Cornea | Fibroblast-like |
| Vero | CCL81 | Monkey Kidney | Fibroblast-like |

Representative of cell culture media which may be used are:
Hank's Minimum Essential Medium,
Earle's Minimum Essential Medium and
Dulbecco's.

Tissue cultures infected with HSV demonstrate characteristic cytological changes including cell enlargement and rounding, ultimately resulting in lysis of infected cells. Infective viruses spill into the culture medium leading to infection of other cells in the culture. Although such cytopathic effect is characteristic for the virus and the cell type involved, this is a subjective assessment, and confirmatory procedures are required. When CPE is observed, there is an elevation of virus concentration in the culture medium which is detectable by the method of the invention. The inoculated tissue cultures should be inoculated using conventional and known techniques. Most viral isolation procedures suggest inoculation of single tubes of two different cell lines; see Lennette, D. A. et al. (1980), supra. and Lennette, D. A. et al. (1981), supra.

The incubating cell cultures should be examined for cytopathic effect (CPE) every 24 hours for up to 7 days. When CPE is observed or at 7 days, one aseptically removes 0.05 ml of the supernatant culture medium and places it onto one circle of a test card such as the one shown in the accompanying drawing. If the culture fluid is turbid and exhibits obvious debris, centrifuge it at 1000 g for 3-4 minutes and take the sample from the clarified supernatent fluid.

Positive and negative controls are applied to adjacent circles on the card and the samples are spread within the confines of the circle using a separate spreader for each. One drop (approximately 15 ul) of reagent charcoal anti-HSV is dispensed into each circle, and the card is rotated for 15 minutes. Agglutination of the charcoal particles in the test specimen circle is confirmatory for HSV-induced CPE. No agglutination in the negative control circle and agglutination in the positive control circle is indicative of appropriate function of the reagent. The negative control may be 0.05 ml of sterile tissue culture medium. It is recommended that CPE positive samples demonstrating negative agglutination be returned to incubation until a CPE of greater than 70% is evident and then retested. If no agglutination is evident at this point, the samples may be considered negative for HSV.

The Herpes Agglutination Test makes use of polyclonal, rabbit anti-herpes antibody adsorbed onto finely-divided, activated charcoal. The particle size is such that negative samples give a homogeneous, gray appearance. Reactive samples cause the charcoal to aggregate, thus forming macroscopically visible, black particles in a clear background. In this assay confirming the presence of HSV, strength of reaction is insignificant, and any agglutination is reported as positive for HSV. The antibody is prepared against herpes simplex virus type 2, strain MS, but possesses known cross-reactivity with HSV type 1; see Zweig, M., C. J. Heilman, Jr., S. V. Bladen, S. D. Showalter, and B. Hampar. 1982. Detection in antisera of antibodies that cross-react with herpes simplex virus type 1 glycoprotein gC. *Inf. and Imm.* 41(1):482-487.

The following preparations and examples describe the manner and process for making and using the invention and set forth the best mode contemplated by the inventors of carrying out the invention but are not to be construed as limiting. All parts given are by weight unless otherwise indicated.

PREPARATION 1

Preparation of Charcoal Reagent

The HSV-II antibody used was purchased from the Dako Corporation in Santa Barbara, California (#B116). All reagents were titered for optimum sensitivity and readability prior to the study. To prepare the HAT reagent, 0.4 mg of the Dako antibody was added to 0.5 ml of lecithin (0.01%) and cholesterol (0.045%) in 95% ethanol. Immediately 0.5 ml of 0.1M phosphate buffered saline (PBS) of pH 7.2 was added and mixed gently. The resulting emulsion was incubated for 25 minutes at room temperature and centrifuged for 10 minutes at 2000 g. The supernatant was decanted without disturbing the pellet. One ml of PBS containing 0.0125M ethylenediaminetetraacetic acid (EDTA) and 0.1% sodium azide was added to resuspend the pellet. Separately, 0.1 ml of a 0.19% suspension of finely-ground activated, aqueous charcoal was added to the above resuspended pellet. The suspension was mixed and gently sonicated to break up charcoal aggregates, and the reagent was refrigerated until used. The reagent is allowed to come to room temperature prior to use as described in the following examples.

PREPARATION 2

Positive Control

Herpes Simples Virus, type 2, Strain G (ATCC VR-734) in supernatant fluid from HSV-infected vero cells cultured in Earle's Minimal Essential Medium with 2% fetal calf serum is provided. HSV in a positive control is inactivated by exposure to a pH 3.5 for thirty minutes at 30° C. The medium is then readjusted to pH 7.2. 0.1% Sodium Azide as Preservative is added. The control is stored at 2°-8° C. Allow reagent to warm to room temperature prior to use in the test.

EXAMPLE 1

Specimens

A total of four-hundred and fifty-one clinical specimens were obtained from two medical laboratories.

Specimens were predominately urogenital, with others from various sites including arm, finger, cheek, eye, buttocks, leg, lip, ear, throat, and back. All specimens were obtained from patients exhibiting lesions.

Isolation

Cotton swabs were used to sample the suspect lesions, then placed into 1.5 to 2.0 ml of transport medium; i.e., brain heart infusion or sucrose phosphate media with 30 ug/ml micostatin and 100 ug/ml gentamycin. Specimens were either sent directly to the virology laboratory or refrigerated until transport. In the lab, specimens were vortexed and inoculated into appropriate cell cultures. At one laboratory (LAB. B) 0.2 ml of the respective supernatant was inoculated onto monolayers of human foreskin fibroblasts and BSC-1 cells (ATCC #CCL 26). The other laboratory (LAB. A) inoculated 0.2 ml of the prepared specimens onto monolayers of Vero (ATCC #CCL 171), and Flow 7000 (human embryonic foreskin). The remainder of each specimen was frozen at −70° C. Cultures contained 2 ml of minimum essential media with 2% fetal bovine serum and were incubated at 37° C.

LAB. A examined cultures daily for characteristic HSV induced cytopathic effect (CPE). Positive cultures were frozen at −70° C. the day CPE was observed. Cultures were considered negative if no CPE was present after 7 days. All cultures were coded and frozen for testing by the HAT method of the invention. The LAB B tested cultures with the HAT Prior to observing CPE. Cultures were considered negative if CPE was not present after seven days. In both laboratories, positive HSV confirmation was determined by inoculating various cell cultures susceptible for isolation of HSV. At LAB. B any isolate exhibiting uncharacteristic CPE or CPE in only one cell line was confirmed by specific immunofluorescence staining. The majority of the isolates received from LAB. A were confirmed by either of two commercially-available HSV immunofluoresence tests (Syva or ENI) or Ortho Diagnostics' HSV ELISA.

Testing Clinical Isolates

Isolates received from LAB. A were thawed at room temperature, vortexed at medium speed, and then centrifuged at 2000 rpm for five minutes. The HAT was performed by aseptically pipetting 50 ul of the culture supernatant from each culture onto an 18 mm circle of a white, particle agglutination card (Hynson, Westcott, and Dunning #8720-D1). Fifty microlites of the positive and negative controls were run with each card. The positive control was prepared by inoculating Vero cells with HSV-II (MS) and allowing 50% CPE. Cells were lysed via freeze-thaw, and the centrifuged supernatant was used as the positive control. The negative control used at both LAB. A and LAB. B was culture medium from uninoculated cell cultures. Each sample was spread using a separate, clean, flat toothpick. The charcoal reagent was vortexed vigorously for 2×5 second intervals before adding 10 ul to each sample. Each card was rotated by hand three to four times and then placed under a humidifier cover on a mechanical card rotator (approximately 100 rpm). Cards were read after a fifteen minute incubation. Following the incubation, the card was rotated manually three to four times to aid in the visualization of the agglutination. An agglutination is judged negative if the charcoal demonstrates a smooth, homogeneous, gray appearance. A positive test exhibits macroscopically visible, black aggregates of charcoal. The aggregates can range from a grainy appearance to very obvious black particles. During the course of this study, strength of agglutination was ranked as negative or +1 to +4 with +4 being the strongest agglutination. There were only two possible reports with the HAT, positive or negative. Weakly positive results, more positive than the negative control, were reported as positive.

Clinical Evaluations

The results of the 451 clinical isolates tested are given in Table 1 below. In comparing the data obtained from both laboratories, it is evident that a freeze-thaw and centrifugation treatment of the cultures from Laboratory A improved the HAT's sensitivity and specificity. The HAT correctly identified 168 of 170 (98.5%) of the treated cultures, exhibiting one false negative and one false positive. The false positive reaction recorded was eliminated by centrifuging the culture. It was found that the presence of extraneous debris in the cell cultures or lysates could cause false positive results. This problem is alleviated by centrifuging the cell lysate or cell culture media exhibiting extraneous debris at 2000 g for five minutes and utilizing the clarified supernatant. As a result of these findings, a specificity control such as charcoal particle coated with a negative serum can be avoided if the HAT is performed on centrifuged cell lysates or cultures showing little or no debris in the supernatant.

Of the 281 untreated cultures tested at LAB. B, 267 of 281 (95.0%) cultures were correctly identified.

TABLE 1

Performance Characteristics of the Herpes Agglutination Test As Compared to Cell Culture Cytopathic Effect (Based on Evaluation of 451 Specimens).

| Lab. Site | Sensitivity (%) | Specificity (%) | Positive Predictive Value | Negative Predictive Value |
|---|---|---|---|---|
| A | 107/108 (99.1%) | 61/62 (98.4%) | 99.1% | 98.4% |
| B | 153/163 (94.0%) | 111/118 (96.6%) | 97.6% | 92.2% |
| TOTAL | 260/271 (95.9%) | 175/180 (97.2%) | 98.4% | 95.3% |

EXAMPLE 2

Comparison to Commercially-Available Kits

Three commercially-available confirmation tests were compared to the HAT On 108 HSV cultures received from LAB. A. All tests were run according to the manufacturer's procedures for viral cultures. Tests used were monoclonal immunofluorescence tests from Syva (Palo Alto, California) and Electronucleonics (ENI, Columbia, Maryland) and Ortho Diagnostics' ELISA (Raritan, New Jersey).

Results presented in Table 2 below, demonstrate a percent agreement of 100%, 97.0%, and 97.8% to the three tests, respectively, for an overall correlation of 98.1%.

TABLE 2

| Test | Total Samples | Sensitivity | Specificity | Positive Predictive Value | Negative Predictive Value |
|---|---|---|---|---|---|
| Syva[1] | 30 | 18/18[a] (100.0%) | 12/12[b] (100.0%) | 100.0% | 100.0% |
| ENI[1] | 33 | 22/23 (95.7%) | 10/10 (100.0%) | 100.0% | 91.0% |
| Ortho[2] | 45 | 21/21 (100.0%) | 23/24 (95.8%) | 95.4% | 100.0% |
| Total | | 61/62 (98.4%) | 45/46 (97.8%) | 98.4% | 97.9% |

[1]Immunofluorescence Assay
[2]Enzyme-Linked Immunosorbent Assay
[a]Positive HAT/positive commercial test
[b]Negative HAT/negative test From the above Table 2 it may be seen that the HAT correlates well with kits available for confirmation of HSV in tissue culture.

EXAMPLE 3

Lower Limits of Antigen Detection in Lysed and Unlysed Cultures as Compared to CPE An untitered viral stock (HSV-II MS) was diluted in serial ten-fold dilutions to $1 \times 10^{-7}$ Vero cells in thirteen six well culture plates were infected for 1.5 hours with 1 ml of the dilutions $10^{-2}$ to $10^{-7}$. Three separate plates were mock-infected and used as the negative controls. After being washed with PBS, four of the infected plates were overlaid with maintenance medium containing 0.5% agarose. These plates were used to titer the stock virus and read after five days. To the remaining six plates, 3 ml of maintenance media was added per well. Cultures were incubated in 5% $CO_2$ at 36° C.

At twenty-four, forty-eight, and seventy-two hours post-infection, two of the infected plates were removed, and 1 ml of cell-free supernatant was aliquoted from each dilution and saved in separate test tubes. The aliquots and their respective cultures were frozen at −70° C. until tested. The aliquots were considered as untreated cultures while the remainder of the cultures (frozen cells) were designated as cell lysates. One mock-infected culture was treated as above at each time period.

RESULTS

Detection Limits of the HAT

The limits of viable HSV antigen detection were determined. Titered stocks of HSV-I (F) and HSV-II (MS) were serially diluted and tested by the method of the invention. The method produced produced easily visible +1 agglutinations down to $6.3 \times 10^4$ pfu/ml of HSV-I (F) and $1.1 \times 10^4$ pfu/ml of HSV-II (MS). Therefore, the HAT detected $3.2 \times 10^3$ pfu/50 ul and $5.5 \times 10^2$ pfu/50 ul of HSV-I (F) and HSV-II (MS), respectively. The actual number of physical virus particles (infectious and non-infectious) was not determined. Cytopathic effect was recorded at each time period before processing the plates. Cell monolayer CPE was granted from 0 to +4, depending on the extent of infection. On plaque to less than 25% cell involvement was graded 1+; 25-49%, 2+; 50-74%, 3+; 75-100%, 4+.

Both the untreated culture supernatant and the cell lysate were thawed at room temperature. The lysates were transferred to separate tests tubes and centrifuged at 2000 g for ten minutes. HAT testing was performed as described.

The lower limits of antigen detection in treated and untreated cell cultures were compared to CPE in TABLE 3 below. Lysing the cells increased the sensitivity of the HAT $10^2$-$10^3$ times and greatly enhanced readability of the agglutination reaction. This test detected HSV antigen in cell lysates before CPE at 24 and 48 hours post-inoculation. This assay detected an infective dose of 44 pfu's in cell lysates at 24 hours and 4.4 pfu's at 48 hours.

TABLE 3

Lower Limits of Detection of the HAT in Lysed and Unlysed Cell Cultures as Compared to CPE at 24 and 48 Hours Postinoculation[a].

| Virus Dilution[b] | Infective Dose (pfu/well) | 24 CPE | 24 HAT(U)[c] | 24 HAT(L)[c] | 48 CPE | 48 HAT(U) | 48 HAT(L) | 72 CPE | 72 HAT(U) | 72 HAT(L) |
|---|---|---|---|---|---|---|---|---|---|---|
| $10^{-2}$ | $4.4 \times 10^4$ | 2+ | 2+ | 4+ | 4+ | 3+ | 4+ | 4+ | 3.5+ | 4+ |
| $10^{-3}$ | $4.4 \times 10^3$ | 1+ | — | 4+ | 4+ | 2+ | 4+ | 4+ | 2.5+ | 4+ |
| $10^{-4}$ | $4.4 \times 10^2$ | 1+ | — | 2+ | 2+ | 1+ | 4+ | 3+ | 2+ | 4+ |
| $10^{-5}$ | $4.4 \times 10^1$ | — | — | 1+ | 1+ | — | 3+ | 1+ | 1+ | 4+ |
| $10^{-6}$ | $4.4 \times 10^0$ | — | — | — | — | — | 2+ | 1+ | — | 2.5+ |
| $10^{-7}$ | $4.4 \times 10^{-1}$ | — | — | — | — | — | — | — | — | — |
| Neg. Ctrl. | 0 | — | — | — | — | — | — | — | — | — |

[a]Results based on duplicate plates.
[b]Dilution of stock virus used to inoculate cultures.
[c]U = unlysed; L = lysed.

The method of the invention demonstrated no prozone effect when using 100% HSV-I or HSV-II infected cell supernatants or lysates. A partial prozone effect was employed when using sonicates of HSV-II infected cells. As with some immunoassays, the possibility of a prozone effect may be exhibited by agglutination tests. This must be considered in the presence of high percentage CPE and negative agglutination. This can be excluded by using the tissue culture medium as diluent, performing 1:10 and 1:100 dilutions of culture medium directly on the card and performing the test again. Positive reactions in the diluted samples demonstrate a positive test. Although this possibility exists, it has never been encountered in our clinical trials. No discernible difference in agglutinations were observed when comparing infective HSV virus to UV inactivated viruses.

Although the above described preferred embodiments of the method of the invention have been described in reference to the detection and immunoassay of antigens associated with viral infection, it will be appreciated that by use of an antigen/surfactant/particle complex reagent, one can immunoassay for the immunological homolog, i.e.; the related antibody. This is useful to monitor a patient for re-infection by observing the antibody titer.

What is claimed:

1. A method of determining the presence or the absence of a viral antigen or an antibody specific for a viral antigen in a biological fluid, which comprises;
    A. providing an extra-corporeal specimen of the biological fluid;
    B. providing an aqueous dispersion of solid, porous carrier particles having adsorbed thereon a complex of the formula:

Ⓐ X-Y wherein X represents a hydrophilic, polar moiety, Y represents a hydrophobic non-polar moiety and Ⓐ is the immunological binding partner of the viral antigen or antibody specific for a viral antigen being determined for; X-Y being a phospholipid surfacant compound and the X-Y compound is complexed with Ⓐ such that the X moiety is oriented toward the polar Ⓐ moiety and the Y moiety is oriented away from the polar Ⓐ moiety and towards the particle;
    C. admixing the specimen provided with the aqueous disperison; and
    D. observing the admixture for an agglutination reaction;

wherein a positive agglutination reaction is indicative of the presence of the viral antigen or the antibody specific for a viral antigen and the absence of an agglutination reaction is indicative of the absence of the viral antigen or the antibody specific for a viral antigen in the biological fluid.

2. The method of claim 1 wherein the carrier particles are of non-polar materials.

3. The method of claim 1 wherein the carrier particles have an average size within the range of from 0.5 to 20 $\mu$m.

4. The method of claim 1 wherein the concentration of the carrier particles in the dispersion is within the range of from about 0.005 to 0.5 percent by weight.

5. The method of claim 1 wherein the carrier particles are activated charcoal.

6. The method of claim 1 wherein the admixture of serum and aqueous dispersion is incubated at a temperature or circa 20° C. to 37° C.

7. The method of claim 1 wherein the viral antigen is an antigen associated with herpes simplex virus.

8. A method of determining the presence or absence of a viral associated antigen in a biological cell culture, which comprises;
    A. providing an aqueous dispersion of charcoal particles having adsorbed thereon a complex of (i) a surfactant of the formula:

X-Y wherein X represents a hydrophilic, polar moiety and Y represents a hydrophobic, non-polar, moiety, said X-Y being a phospholipid surfactant compound, and (ii) the antibody which is immunoreactive with said antigen; said complex being such that the X moiety is oriented toward the antibody and the Y moiety is oriented away from the antibody and toward the particle;
    B. admixing a specimen of fluid from the culture with the aqueous dispersion; and
    C. observing the mixture obtained for an agglutination reaction;

wherein a positive reaction is indicative of the presence of said antigen and a negative reaction is indicative of the absence of said antigen.

* * * * *